(12) United States Patent
Bao et al.

(10) Patent No.: US 12,215,079 B2
(45) Date of Patent: Feb. 4, 2025

(54) METHOD FOR SEPARATING MIXED XYLENE

(71) Applicant: ZHEJIANG UNIVERSITY, Zhejiang (CN)

(72) Inventors: Zongbi Bao, Zhejiang (CN); Liangying Li, Zhejiang (CN); Qilong Ren, Zhejiang (CN); Lidong Guo, Zhejiang (CN); Qiwei Yang, Zhejiang (CN); Zhiguo Zhang, Zhejiang (CN); Yiwen Yang, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 163 days.

(21) Appl. No.: 17/999,200

(22) PCT Filed: Feb. 3, 2021

(86) PCT No.: PCT/CN2021/075102
§ 371 (c)(1),
(2) Date: Nov. 17, 2022

(87) PCT Pub. No.: WO2022/165677
PCT Pub. Date: Aug. 11, 2022

(65) Prior Publication Data
US 2023/0257328 A1   Aug. 17, 2023

(51) Int. Cl.
*C07C 7/12* (2006.01)
*B01J 20/22* (2006.01)
(Continued)

(52) U.S. Cl.
CPC .............. *C07C 7/12* (2013.01); *B01J 20/226* (2013.01); *B01J 20/28061* (2013.01);
(Continued)

(58) Field of Classification Search
CPC ...... C07C 7/12; C07C 2601/16; B01J 20/226; B01J 20/28061; B01J 20/2808;
(Continued)

(56) References Cited

U.S. PATENT DOCUMENTS

2016/0159713 A1* 6/2016 Long ............... B01J 20/226
585/830

FOREIGN PATENT DOCUMENTS

| CN | 108993417 A | 12/2018 |
| CN | 109107329 A | 1/2019 |

(Continued)

OTHER PUBLICATIONS

Ashok Yadav et al., "Anilate Tethered Neutral Tetrahedral Pd(II) Cages Exhibiting Selective Encapsulation of Xylenes and Mesitylene", Chemistry—A European Journal, vol. 26, No. 19, Feb. 18, 2020, pp. 4209-4213.

*Primary Examiner* — Prem C Singh
*Assistant Examiner* — Francis C Campanell
(74) *Attorney, Agent, or Firm* — NKL Law; Bin Lu

(57) ABSTRACT

A method for separating mixed xylene includes steps that the mixed xylene is subjected to adsorption separation by means of an adsorbent having a metal organic framework material, so that one or more of xylene isomers are separated out. An organic ligand in the metal organic framework material is 2,5-dihydroxy-1,4-benzoquinone. Xylene isomers can be effectively separated using this method.

17 Claims, 9 Drawing Sheets

(51) Int. Cl.
*B01J 20/28* (2006.01)
*B01J 20/34* (2006.01)

(52) U.S. Cl.
CPC ....... *B01J 20/2808* (2013.01); *B01J 20/3483* (2013.01); *B01J 2220/56* (2013.01); *C07C 2601/16* (2017.05)

(58) Field of Classification Search
CPC ............... B01J 20/3483; B01J 2220/56; B01J 20/28057; B01J 20/28078; B01J 20/3433; B01D 2253/204; B01D 2256/24; B01D 2257/7027; B01D 2259/40088; B01D 15/1821; B01D 53/02
USPC ........................................................ 585/830
See application file for complete search history.

(56) References Cited

FOREIGN PATENT DOCUMENTS

| | | |
|---|---|---|
| JP | 2017014146 A | 1/2017 |
| WO | 2012012125 A2 | 1/2012 |
| WO | 2017048378 A1 | 3/2017 |

\* cited by examiner

METHOD FOR SEPARATING MIXED XYLENE

FIELD OF THE INVENTION

The present invention relates to a method for separating mixed xylenes.

BACKGROUND OF THE INVENTION

Various xylene isomers in mixed xylenes, including para-xylene (PX), ortho-xylene (OX), and meta-xylene (MX), are all very important feedstocks for industrial synthesis. For example, para-xylene (PX) is an important organic chemical feedstock used primarily for synthesis of terephthalic acid (PTA) or dimethyl terephthalate (DMT) which is then used for producing polyethylene glycol terephthalate (PET). PET, due to its excellent properties, is widely used in manufacture of fibers, films, and resins and is a very important raw material for synthesis of fibers and plastics. Ortho-xylene (OX) is used primarily for producing chemical products such as phthalic anhydride (PA), dyes, pesticides, and the like, and its derivative ortho-phthalaldehyde can be used to prepare phthalate plasticizers. Meta-xylene (MX) is used primarily as an intermediate in pharmaceuticals, perfumes and dyes and as an oil-soluble color-former for color films. While single-component xylene isomers are widely used in various chemical and pharmaceutical fields, it remains an unsolved problem that it is extremely difficult to separate mixed xylenes to obtain single-component xylene isomers, because components (para-xylene, meta-xylene, ortho-xylene) in mixed xylenes have very close densities, very slightly different boiling points (para-xylene has a boiling point of 138.5° C.; ortho-xylene has a boiling point of 144.4° C.; and meta-xylene has a boiling point of 139.2° C.), and very close molecular kinetic sizes (para-xylene has a molecular kinetic size of 5.8 Å; ortho-xylene has a molecular kinetic size of 6.8 Å; and meta-xylene has a molecular kinetic size of 6.8 Å).

At present in industry, there are few methods for efficient separation of mixed xylenes. These mainly comprise precision rectification methods, low-temperature atmospheric crystallization methods, cryogenic crystallization methods, and pressurized crystallization methods, complexing methods, and adsorptive separation methods. The precision rectification methods involve continuous rectification operations in multiple columns. The equipment required for precision rectification is expensive, complicated to operate, and unable to completely separate out meta-xylene and para-xylene. Huge energy consumption produced during rectification and its unsuitability to medium and small scale equipment also limits the popularity and use of precision rectification. The low-temperature atmospheric crystallization methods, by mainly using differences in freezing points and solubility of the isomers in the mixture at atmospheric pressure, enable the isomers to precipitate respectively at different temperature sections. However, mixed xylenes are a mixed system of multiple liquid phases, in which case solid-liquid phase diagrams of isomers overlap; it is therefore difficult to obtain single-component xylene isomers at a single temperature. The cryogenic crystallization or pressurized crystallization methods, by using also differences in physical and chemical properties of isomers, especially differences in freezing points of the isomers, separates mixed xylenes by pressurization or temperature reduction depending on different phase transitions. Separation by this method can be completed in a short period of time, and the whole process is low energy-consuming and easy to operate, but has a high requirement for equipment and operations due to the required conditions of high pressure and extremely low temperature. The method is thus undesirable in practical production. The complexing extraction method is a process that utilizes the basicity of hydrocarbons and the acidity of a complexing extractant to form an acid-base complex to thereby realize separation. Atypical complexing agent is $HF-BF_3$. There is a significant difference in relative basicity of the three isomers in mixed xylenes. For example, if the relative basicity of para-xylene is 1, then the relative basicity of ortho-xylene is 2, and the relative basicity of meta-xylene is 100. It is therefore possible to separate out single-component xylene isomers from mixed xylenes by using the difference in relative basicity. The complexing agent in this method, however, not only acts as a complexing extractant, but also acts as a catalyst for liquid phase isomerization reaction. The method is thus complicated to operate and recovery of the complexing agent consumes too much energy.

It is therefore desirable to provide a more economical and energy efficient separation means for separation and purification of para-xylene, ortho-xylene, and meta-xylene. Comparatively speaking, adsorptive separation is characterized by simple operation, low energy consumption, low cost, etc., but what is most critical in adsorptive separation of mixed xylenes is the selection of an adsorbent having excellent adsorbing capacity and high adsorption selectivity. Common adsorbents comprise activated carbons, clays, molecular sieves, silica gels, etc. Such materials, however, due to their uniform internal pore structures and inconvenience to modify chemical environments of the pores, are not able to reach an industrial application level in terms of their adsorption capacity and separation selectivity.

SUMMARY OF THE INVENTION

The inventors of the present invention discovered through a large amount of research that a special metal-organic framework material has high adsorption selectivity for xylene isomers (ortho-xylene, meta-xylene, and para-xylene) and thus can be used to effectively separate pure isomer components from mixed xylenes. The present invention is thus proposed on the basis of this discovery.

The present invention provides a method for separating mixed xylenes. The method comprises subjecting the mixed xylenes to adsorptive separation by an adsorbent containing a metal-organic framework material to separate out one or more xylene isomers. The metal-organic framework material comprises an organic ligand which is 2,5-dihydroxy-1,4-benzoquinone.

In the present invention, the term "mixed xylenes" refers to a mixture comprising two or three xylene isomers. The "mixed xylenes" may also comprise other components such as ethylbenzene, styrene, toluene, benzene, etc., in addition to xylene isomers. According to some embodiments, the mixed xylenes comprise more than 80% of xylene isomers. According to some embodiments, the mixed xylenes comprise more than 90% of xylene isomers. According to some embodiments, the mixed xylenes comprise 95% or more of xylene isomers.

In the present invention, the term "xylene isomers" refer to ortho-xylene, meta-xylene, and para-xylene.

According to some embodiments, the mixed xylenes comprise para-xylene which may be present at a content of 5%-95%. According to some embodiments of the present invention, para-xylene is present in the mixed xylenes at a volume of between 5%-95%. Preferably, para-xylene is present in the mixed xylenes vapor or mixed xylenes liquid at a volume of 10%-85%. According to some embodiments, para-xylene is present in the mixed xylenes at a volume of 5%, 15%, 25%, 35%, 50%, 60%, 70%, 80%, or 90%.

According to some embodiments, the mixed xylenes comprise para-xylene and ortho-xylene. According to some embodiments, the mixed xylenes comprise para-xylene and meta-xylene. According to some embodiments, the mixed xylenes comprise para-xylene, meta-xylene, and ortho-xylene. According to some embodiments of the present invention, the mixed xylenes comprise ortho-xylene and para-xylene.

According to some embodiments of the present invention, the metal ions in the metal-organic framework material are selected from transition metal ions and alkaline earth metal ions.

According to some embodiments of the present invention, the metal ions in the metal-organic framework material are selected from transition metal ions and alkaline earth metal ions.

According to some embodiments of the present invention, the metal ions comprise one or more selected from the group consisting of zinc ions, manganese ions, cobalt ions, magnesium ions, vanadium ions, zirconium ions, calcium ions, molybdenum ions, chromium ions, iron ions, nickel ions, copper ions, tin ions, niobium ions, titanium ions, and scandium ions.

According to some preferred embodiments of the present invention, the metal ions comprise one or more selected from the group consisting of zinc ions, cobalt ions, magnesium ions, and manganese ions.

According to some more preferred embodiments of the present invention, the metal ions comprise manganese ions.

According to some embodiments of the present invention, the metal-organic framework material has a pore size of 4 Å or more, preferably 4 Å-15 Å. More preferably, the metal-organic framework material has a pore size of 4 Å-10 Å.

According to some preferred embodiments of the present invention, the metal-organic framework material has a specific surface area of 300 m$^2$/g-2000 m$^2$/g, for example, 300 m$^2$/g-1000 m$^2$/g.

According to some embodiments of the present invention, the adsorptive separation is performed at a temperature of −5° C.-300° C., preferably 25° C.-250° C., and more preferably 30° C.-150° C.

According to some embodiments of the present invention, the adsorptive separation is performed at a pressure of 0.01 MPa-10 MPa, preferably 0.1 MPa-6 MPa.

According to some embodiments of the present invention, the adsorptive separation is performed using a fixed bed, and the adsorbent is packed in the adsorption column of the fixed bed, and may specifically comprise the following steps: (1) passing a mixed xylenes vapor formed by the mixed xylenes and a carrier gas through the adsorption column of the fixed bed, so that a strongly adsorbed xylene isomer in the mixed xylenes is adsorbed on the adsorbent and a weakly adsorbed xylene isomer in the mixed xylenes passes through the adsorption column, thereby obtaining the weakly adsorbed xylene isomer; and (2) desorbing the strongly adsorbed xylene isomer from the adsorbent to obtain the strongly adsorbed xylene isomer. According to some embodiments, in step (1), the strongly adsorbed xylene isomer is para-xylene, and the weakly adsorbed xylene isomer is ortho-xylene and/or meta-xylene. According to some preferred embodiments of the present invention, the mixed xylenes vapor is passed through the adsorption column of the fixed bed at a flow rate of 40 mL/min/g-200 mL/min/g adsorbent.

According to some embodiments of the present invention, the adsorptive separation is performed using a simulated moving bed, the adsorbent being packed in adsorption zone beds of the simulated moving bed, and preferably comprises the following step: (3) passing the mixed xylenes liquid through the liquid phase simulated moving bed for adsorptive separation, so as to withdraw para-xylene, ortho-xylene, and/or meta-xylene from different beds. According to some embodiments of the present invention, the simulated moving bed has 4-32 of adsorbent beds, and the ratio of the adsorption zone beds to the desorption zone beds is 1.0-1.5.

According to some embodiments of the present invention, during the adsorptive separation, the adsorbent and the mixed xylenes are at a temperature of −5° C.-300° C., preferably 25° C.-250° C., and more preferably 30° C.-150° C. According to some embodiments, the adsorbent and the mixed xylenes are at a temperature of 30° C., 40° C., 50° C., 60° C., 70° C., 80° C., 90° C., 110° C., or 120° C.

According to some embodiments of the present invention, the mixed xylenes subjected to the adsorptive separation are in the form of a mixed xylenes vapor or liquid. According to some embodiments of the present invention, during the adsorptive separation, the adsorbent and the mixed xylenes vapor are at a pressure of 100 kPa-1200 kPa, preferably 100 kPa-1000 kPa. According to some embodiments, the adsorbent and the mixed xylenes vapor are at a pressure of 100 kPa-600 kPa. According to some embodiments, the adsorbent and the mixed xylenes liquid are at a pressure of 1.1 MPa-2.5 MPa.

According to some embodiments of the present invention, the mixed xylenes vapor consists of the mixed xylenes and a carrier gas. According to some embodiments, the carrier gas is nitrogen and/or helium.

According to some embodiments of the present invention, a weight ratio of the adsorbent to the mixed xylenes is 1-20, preferably 1-10, more preferably 1-5.

According to some embodiments of the present invention, the metal-organic framework material is in the shape of a cube, a needle, or a rod. The metal-organic framework material used in the present invention may be prepared into spherical, columnar, granular adsorptive separation materials or the like by different processing techniques.

According to some embodiments of the present invention, the adsorptive separation is carried out under conditions of altering the total pressure of the mixed xylenes vapor or liquid, or altering the adsorption temperature of the adsorbent, or altering both.

According to some embodiments of the present invention, during the adsorptive separation, the adsorbent is brought to a temperature of from 30° C. to less than 60° C. The inventors have found that when the adsorbent is at a working temperature of less than 60° C., and when ortho-xylene is at a saturation vapor pressure of less than 900 Pa, the interaction between ortho-xylene and the adsorbent is extremely weak and ortho-xylene can be quickly desorbed from the adsorbent, in which case a pure ortho-xylene product can be obtained; while under such conditions, the interaction between meta-xylene/para-xylene and the adsorbent is strong and meta-xylene/para-xylene is retained in the adsorbent for a certain period of time before being desorbed from the adsorbent.

According to some embodiments of the present invention, during the adsorptive separation, the adsorbent is brought to a temperature of from 60° C. to less than 110° C. The inventors have found that when the adsorbent is at a working temperature of more than 60° C. but less than 110° C., the interaction between meta-xylene and the adsorbent is stronger that that between ortho-xylene and the adsorbent, and meta-xylene can thus be retained longer in the adsorbent before exiting, in which case a pure component meta-xylene product can be harvested; under such conditions, the interaction between para-xylene and the adsorbent is the strongest, and it is after the adsorption saturates that para-xylene is finally desorbed slowly from the adsorbent, in which case pure component para-xylene can be obtained.

According to some embodiments of the present invention, during the adsorptive separation, the adsorbent is brought to a temperature of 110° C.-200° C., preferably 110° C.-150° C., to separate out para-xylene. The inventors have found that when the adsorbent is at a working temperature of over 110° C., the interaction between ortho-xylene/meta-xylene and the adsorbent is weak, and ortho-xylene/meta-xylene can quickly precipitate after being retained in the adsorbent for a relatively short period of time, while the interaction between para-xylene and the adsorbent is still strong, by way of a single product can be obtained due to different retention time.

The adsorptive separation of the present invention is simple in its method, which involves simply passing a mixed vapor or a mixed liquid at a certain pressure through an adsorption tower or adsorption column packed with the adsorbent. Further, provided may be one or more adsorption columns, and separation is realized by existing pressure swing adsorption or vacuum pressure swing adsorption or temperature swing adsorption.

According to some embodiments of the present invention, the method further comprises regenerating the adsorbent after the adsorptive separation is completed. Preferably, the regenerating comprises heating the adsorbent to a temperature of 50° C.-300° C. under vacuum or inert atmosphere and keeping the adsorbent at the temperature for 20 hours-120 hours. A too high temperature or a too long period of time would cause structural damage to the adsorbent; and a too low temperature or a too short period of time would make it impossible to completely remove a residual adsorbate from the adsorbent.

According to the present invention, the metal-organic framework material is a three-dimensional or two-dimensional network frame structure formed from transition metal ions or alkaline earth metal ions and an organic ligand (2,5-dihydroxy-1,4-benzoquinone) via coordination bonds or intermolecular forces.

In the present invention, the geometry of pores in the metal-organic framework material used is adaptive at different temperatures to the geometry of molecules of a corresponding xylene, and the material has a network-like structure formed by a layered framework through hydrogen bonding between layers. A layered plane formed from the coordination of ligand molecules in the material with the metal ions contains a large amount of 7r electron cloud, which forms 7r-7r electron cloud accumulation with benzene ring planes of para-xylene, ortho-xylene, and meta-xylene, thereby leading to strong interaction. Due to the geometry and linear structure of para-xylene molecules, strong interaction is formed between the molecules and the layered surface and adapted pores of the material. Thermodynamic and kinetic results show that these two factors result in a significant difference in adsorbed amounts of molecules of the three xylene isomers on the surface of the material. When the mixed vapor or mixed liquid is passed through the adsorption column, the interaction between ortho-xylene and the adsorbent is the weakest and the adsorbed amount of ortho-xylene is the smallest, and therefore ortho-xylene is the first to exit from the adsorbent or the adsorptive separation unit; the interaction between meta-xylene and the adsorbent is stronger and the adsorbed amount of meta-xylene is greater, and therefore compared with ortho-xylene a longer period of time is required for meta-xylene to exit from the adsorbent or the adsorptive separation unit; and the molecular size of para-xylene matches the geometric pore size of the material and adsorbed amount therefore is the greatest, and therefore the longest period of time is required for para-xylene to exit from the adsorbent or the adsorptive separation unit. The three C8 aromatic isomers namely para-xylene, meta-xylene, and ortho-xylene are thus separated out.

According to some embodiments of the present invention, the metal-organic framework material is prepared by a method including the following steps.

(a) An inorganic salt, an organic ligand, and deionized water are mixed and then reacted. The inorganic salt is chloride salt, nitrate, acetate, carbonate, sulfate, or perchlorate of metal ions. The organic ligand is 2,5-dihydroxy-1,4-benzoquinone.

(b) A reaction product resulted in step (a) is washed and dried.

The metal-organic framework material is prepared by reacting 2,5-dihydroxy-1,4-benzoquinone, which is used as an organic ligand, with a range of metal inorganic salts in pure water, without the use of a toxic, volatile organic solvent. The preparation is characterized by low-cost raw materials, mild synthesis conditions, simple operations, easy post-processing, and low-cost material synthesis.

In the method of the present invention, the metal-organic framework material has high adsorption capacity and separation selectivity for para-xylene/meta-xylene, para-xylene/ortho-xylene, and meta-xylene/ortho-xylene, is stable in structure and adsorption performance, has excellent water resistance, and thus has good industrial application prospects.

The adsorbent prepared using the method described above is stable in structure and performance and regular in particle shape, and has a very high separation selectivity and adsorption capacity for mixed xylenes vapor or mixed xylenes liquid.

Further preferably, the molar ratio of the organic ligand to the inorganic salt is 1.(0.5-10). The deionized water, as a solvent, is used at a volume capacity of 10 mL-2000 mL. Further preferably, when the inorganic salt is a cobalt salt, a zinc salt, an iron salt, a manganese salt, a magnesium salt, a calcium salt, a tin salt, or a scandium salt, the molar ratio of the organic ligand to the inorganic salt is 1:(0.5-10), and the deionized water as the solvent, is used at a volume capacity of 10 mL-2000 mL; when the inorganic salt is a zinc salt, a cobalt salt, a magnesium salt, or a manganese salt, the molar ratio of the organic ligand to the inorganic salt is 1:(1-10), and water as the solvent, is used at a volume capacity of 20 mL-2000 mL.

Further preferably, when the inorganic salt is a cobalt salt, a nickel salt, a zinc salt, an iron salt, a manganese salt, a tin salt, or a scandium salt, the ratio of the inorganic salt to the organic ligand to the deionized water is 1 mmol:1 mmol:(5-40) mL; when the metal salt is a magnesium salt or a manganese salt, the ratio of the organic ligand to the inorganic salt to the deionized water is 1.5 mmol:(1.5-6) mmol:(10-2000) mL. A change to the ratio of the metal salt to the organic ligand to the deionized water can change the size, the type, and regularity of crystals, and can also affect the adsorption capacity and separation selectivity of the material for para-xylene, meta-xylene, and ortho-xylene.

Most preferably, when the inorganic salt is zinc acetate dihydrate, cobalt chloride hexahydrate, scandium nitrate hydrate, tin chloride dihydrate, magnesium acetate hydrate, manganese acetate tetrahydrate, and iron chloride hexahydrate, the ratio of the metal salt to the organic ligand to the deionized water is 150 mmol:150 mmol:1000 mL; when the inorganic salt is anhydrous manganese chloride, the ratio of the metal salt to the organic ligand to the deionized water is 4 mmol:3 mmol: 30 mL; and when the inorganic salt is anhydrous magnesium sulfate, the ratio of the metal salt to the organic ligand to the deionized water is 6 mmol:1.5 mmol:400 mL.

According to some embodiments of the present invention, the mixing is performed under stirring at the following conditions: stirring for 5-72 hours at a speed of 200-1000 rpm; and the reaction solution is mixed uniformly for a reaction. Non-uniform mixing or incomplete reaction can lead to irregular morphology of obtained crystals, thereby affecting the adsorptive separation performance of the material for xylene isomers.

Further preferably, the reaction is conducted at a temperature of 10° C.-50° C. for a time period of 5-70 hours, preferably at a temperature of 25° C.-40° C. for a time period of 8-48 hours. The temperature of the reaction affects the generation of crystals, and a too high or too low temperature can lead to failure in generation of the crystals.

According to some embodiments of the present invention, the product resulted after the completion of the reaction is centrifugally washed multiple times with deionized water to replace residual ligand and inorganic salt in the pores.

Further preferably, the thoroughly washed product is activated under vacuum or under inert gas (e.g., nitrogen, helium, etc.) purging at a temperature of 50° C.-250° C. for a time period of 12-24 hours.

Compared with the existing technologies, the present invention has the following advantages.

The organic ligand and the metal salts for preparation of the metal-organic framework material used in the present invention are inexpensive and easily available. The metal-organic framework material can be synthesized at mild conditions and purified with very simple steps, which are easy to operate and amplify.

In the method of the present invention, the metal-organic framework material used is structurally stable, and has very high adsorptive separation selectivity for para-xylene/meta-xylene, para-xylene/ortho-xylene, meta-xylene/ortho-xylene mixed vapor or mixed liquid.

The metal-organic framework material used in the present invention is stable in performance and has adsorption performance that remains the same after multiple cycles of adsorption-regeneration.

In the adsorptive separation of xylene isomers, the adsorbent prepared by the present invention is much better than most of the existing solid adsorbents, and is especially advantageous in the purification of xylene mixing systems to obtain single-component xylenes or in the condensation of single-component xylenes.

DETAILED DESCRIPTION OF THE EMBODIMENTS

The present invention is further described by way of the following embodiments. The present invention however is not limited to these embodiments.

Example 1

300 mmol of zinc acetate dihydrate, 300 mmol of 2,5-dihydroxy-1,4-benzoquinone, and 1000 mL of deionized water were mixed and then reacted under stirring at room temperature for 12-48 hours. After the reaction was completed, the resulting solid product was centrifugally washed multiple times with deionized water until the supernatant was clear to obtain a purified metal-organic framework material. Measurement and analysis of isotherms of $N_2$ adsorption-desorption on the purified metal-organic framework material at 77 K resulted in a specific surface area of 441.7 m$^2$/g and an average pore size of 5.47-5.51 Å. The purified metal-organic framework material was vacuum activated at 150° C. for 12 hours to give a solvent-removed adsorbent. Vapor-phase adsorption of xylene isomers was then tested.

Figure 5:
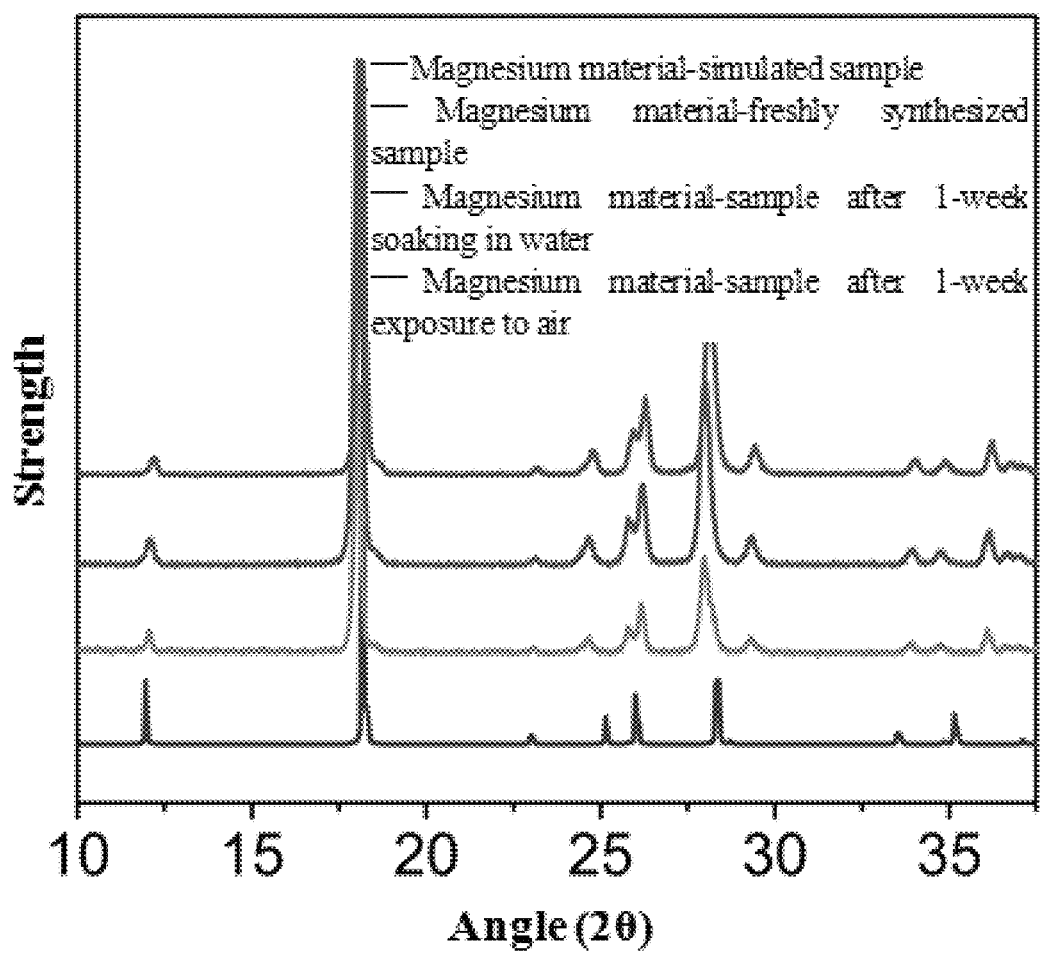
FIG. 5 is an XRD pattern of a metal-organic framework material prepared in Example 4.

In order to test the adsorptive separation performance of the metal-organic framework material synthesized above, isotherms of adsorption of single-component para-xylene, single-component ortho-xylene, and single-component meta-xylene on the above adsorbent were measured. The adsorption was conducted with an appropriate amount of the adsorbent at temperatures of 30° C., 60° C., 90° C., and 120° C., respectively. The test showed that at 30° C. and at a single-component saturation vapor pressure of 1000 Pa, para-xylene was adsorbed by an amount of up to 200 mg/g, ortho-xylene was adsorbed by an amount of only 78 mg/g, and meta-xylene was adsorbed by an amount of only 51 mg/g. Isotherms of adsorption are shown in FIG. 5. At 60° C. and at a single-component saturation vapor pressure of 1000 Pa, para-xylene was adsorbed by an amount of 165 mg/g, ortho-xylene was adsorbed by an amount of 25 mg/g, and meta-xylene was adsorbed by an amount of 30 mg/g. At 90° C. and at a single-component saturation vapor pressure of 1000 Pa, para-xylene was adsorbed by an amount of 66 mg/g, ortho-xylene was adsorbed by an amount of 17 mg/g, and meta-xylene was adsorbed by an amount of 18 mg/g. At 120° C. and at a single-component saturation vapor pressure of 1000 Pa, para-xylene was adsorbed by an amount of 19 mg/g, ortho-xylene was adsorbed by an amount of 22 mg/g, and meta-xylene was adsorbed by an amount of 25 mg/g.

A specific method of separating mixed xylenes with the above synthesized metal-organic framework material is as follows.

The synthesized adsorbent was first molded. An amount of a binder needed in the molding accounted for 3%-10% of a mass of the adsorbent. Breakthrough experiments on a mixed xylenes vapor were conducted using the molded adsorbent. The mixed vapor for adsorptive separation in this example was a mixed vapor of three or two of para-xylene, meta-xylene, and ortho-xylene, with a ratio of saturation vapor pressures of the single-component xylenes being 1:1:1 or 1:1, and a total pressure of the mixed vapor being 0.1 MPa. A packed column had a size of 10 mm I.D.×50 mm, and was packed with about 2.2 g of the molded adsorbent. The test showed that, when the adsorbent was at a temperature of 30° C. and with a saturation vapor pressure ratio of ortho-xylene to meta-xylene to para-xylene was 1:1:1, ortho-xylene and meta-xylene began to pass through the column at 8 minutes, while para-xylene was retained in the packed column for about 120 minutes before beginning to pass through the column. Such a large difference in retention time indicates that the mixed xylenes were effectively separated. After five cycles of adsorption-regeneration, the metal-organic framework material was still stable in its adsorption performance. Conditions for the regeneration were to heat the adsorbent to 150° C. under vacuum or inert atmosphere and keep the adsorbent at the temperature for 72 hours.

Example 2

600 mmol of manganese acetate tetrahydrate, 600 mmol of 2,5-dihydroxy-1,4-benzoquinone, and 2000 mL of deionized water were mixed and then reacted under stirring at room temperature for 24-48 hours. After the reaction was completed, the resulting solid was centrifugally washed multiple times with deionized water to obtain a purified metal-organic framework material. Measurement and analysis of isotherms of $N_2$ adsorption-desorption on the purified metal-organic framework material at 77 K resulted in a specific surface area of 428.9 m$^2$/g and an average pore size of 5.48-5.63 Å. The purified metal-organic framework material was vacuum degassed at 150° C. for 12 hours to give a solvent-removed adsorbent. Vapor-phase adsorption test was then conducted.

Figure 6:
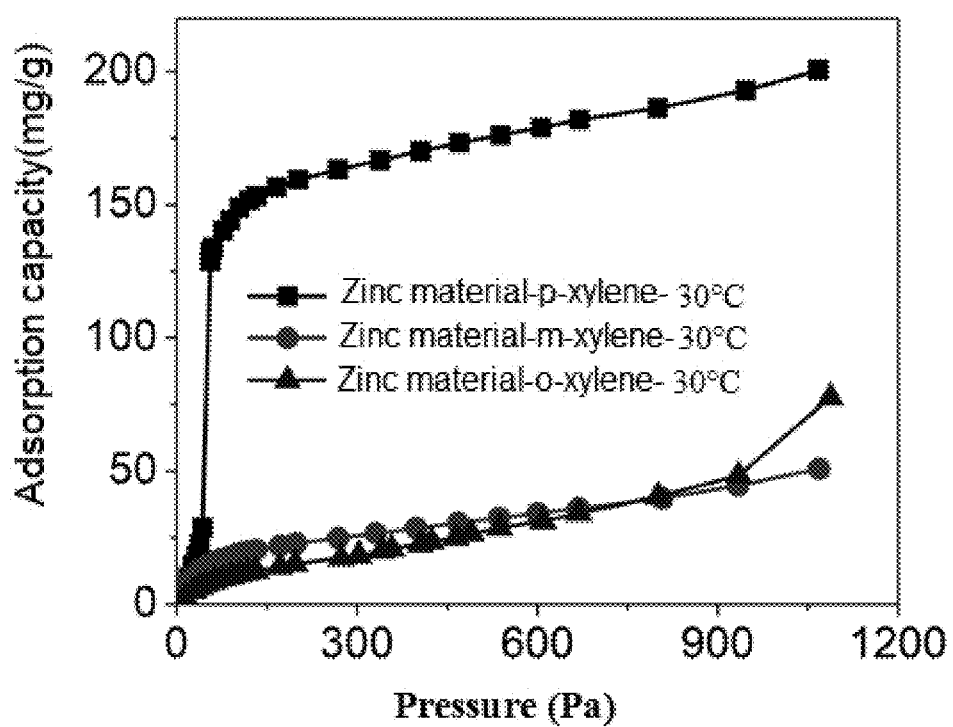
FIG. 6 shows isotherms of adsorption of xylenes on the metal-organic framework material prepared in Example 1 at 30° C.
Figure 7:
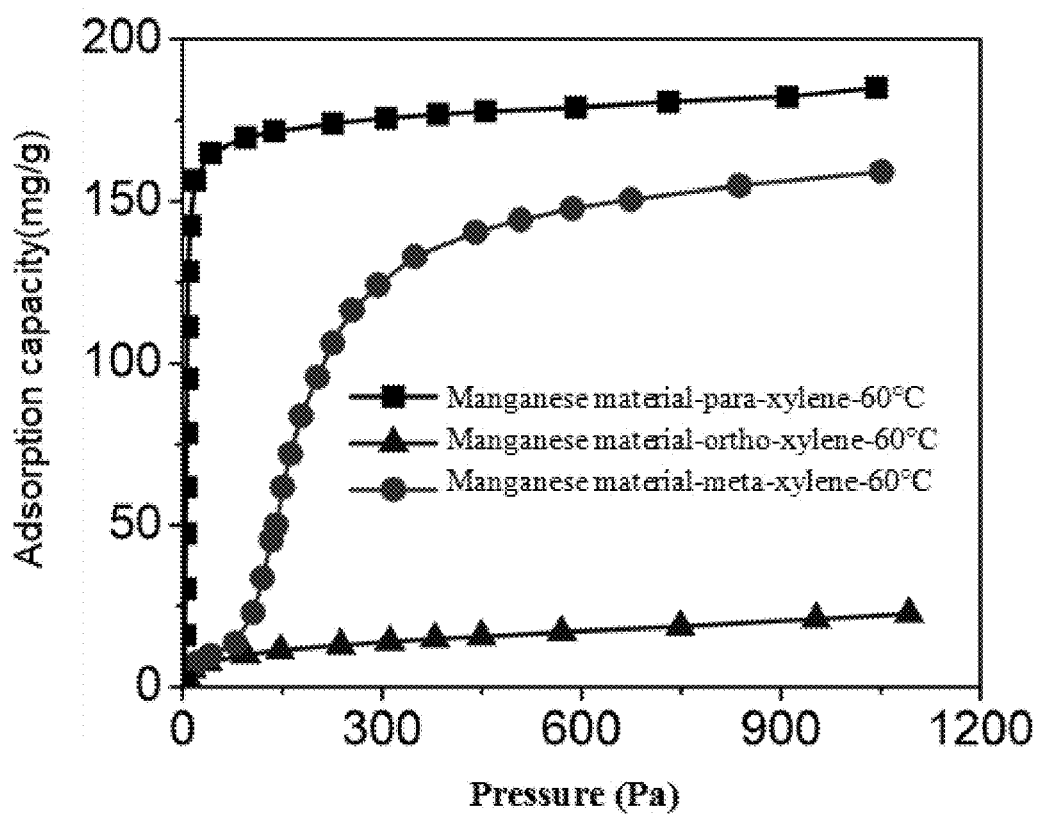
FIG. 7 shows isotherms of adsorption of xylenes on the metal-organic framework material prepared in Example 2 at 60° C.

In order to test the adsorptive separation performance of the metal-organic framework material synthesized above, isotherms of adsorption of single-component para-xylene, single-component ortho-xylene, and single-component meta-xylene on the metal-organic framework material as an adsorbent were measured. The adsorption was conducted with an appropriate amount of the adsorbent at temperatures of 30° C., 60° C., 90° C., and 120° C., respectively. The test showed that at 30° C. and at a single-component saturation vapor pressure of 1000 Pa, para-xylene was adsorbed by an amount of up to 208 mg/g, ortho-xylene was adsorbed by an amount of 170 mg/g, and meta-xylene was adsorbed by an amount of 204 mg/g. At 60° C. and at a single-component saturation vapor pressure of 1000 Pa, para-xylene was adsorbed by an amount of up to 185 mg/g, ortho-xylene was adsorbed by an amount of only 23 mg/g, and meta-xylene was adsorbed by an amount of 159 mg/g. At 90° C. and at a single-component saturation vapor pressure of 1000 Pa, para-xylene was adsorbed by an amount of up to 160 mg/g, ortho-xylene was adsorbed by an amount of only 22 mg/g, and meta-xylene was adsorbed by an amount of 69 mg/g. At 120° C. and at a single-component saturation vapor pressure of 1000 Pa, para-xylene was adsorbed by an amount of up to 141 mg/g, ortho-xylene was adsorbed by an amount of only 23 mg/g, and meta-xylene was adsorbed by an amount of only 17 mg/g. Isotherms of adsorption are shown in FIGS. 6 and 7.

A specific method of separating mixed xylenes with the above synthesized metal-organic framework material is as follows.

Figure 8:
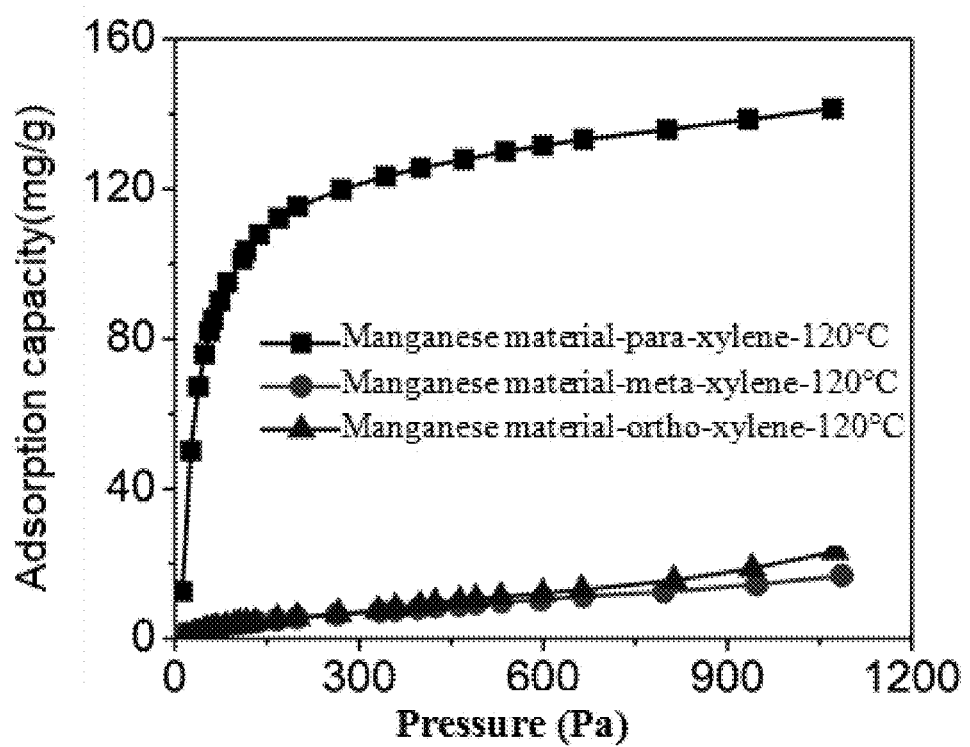
FIG. 8 shows isotherms of adsorption of xylenes on the metal-organic framework material prepared in Example 2 at 120° C.
Figure 9:
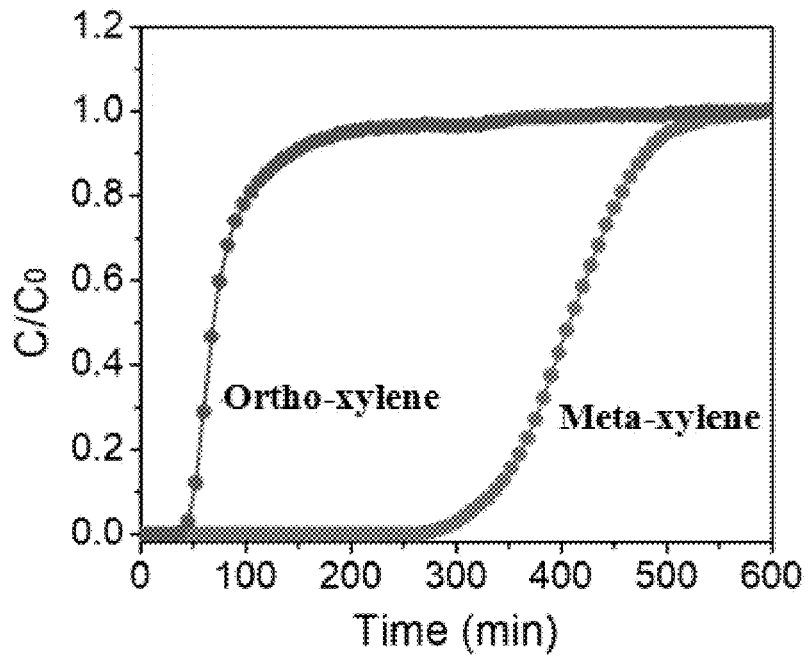
FIG. 9 shows breakthrough curves of ortho-xylene/meta-xylene through the metal-organic framework material prepared in Example 2 at 30° C.

The synthesized adsorbent was first molded. An amount of a binder needed in the molding accounted for 3%-10% of a mass of the adsorbent. Breakthrough experiments on a mixed xylenes vapor were conducted using the molded adsorbent. The mixed vapor for adsorptive separation in this example was a mixed vapor of three or two of para-xylene, meta-xylene, and ortho-xylene, with a ratio of saturation vapor pressures of the single-component xylenes being 1:1:1 or 1:1, and a total pressure of the mixed vapor being 0.1 MPa. A packed column had a size of 10 mm I.D.×50 mm, and was packed with about 2.3 g of the molded adsorbent. Breakthrough curves are shown in FIGS. 8 and 9. The test showed that, when the adsorbent was at a temperature of 30° C. and with a saturation vapor pressure ratio of ortho-xylene to meta-xylene being 50:50, ortho-xylene began to pass through the column at 45 minutes, while meta-xylene began to pass through the column at 275 minutes. Such a large difference in retention time indicates that the two xylene isomers were effectively separated. In addition, when the adsorbent was at a temperature of 90° C. and with a saturation vapor pressure ratio of meta-xylene to para-xylene being 50:50, meta-xylene began to pass through the column at 25 minutes, while para-xylene began to pass through the column at 315 minutes. Such a large difference in retention time indicates that meta-xylene and para-xylene were effectively separated under such conditions. After five cycles of adsorption-regeneration, the metal-organic framework material was still stable in its adsorption performance. Conditions for the regeneration were to heat the adsorbent to 150° C. under vacuum or inert atmosphere and keep the adsorbent at the temperature for 72 hours.

Adsorptive separation was performed on a continuous counter-current small-scale simulated moving bed using the adsorbent described above.

Figure 1:
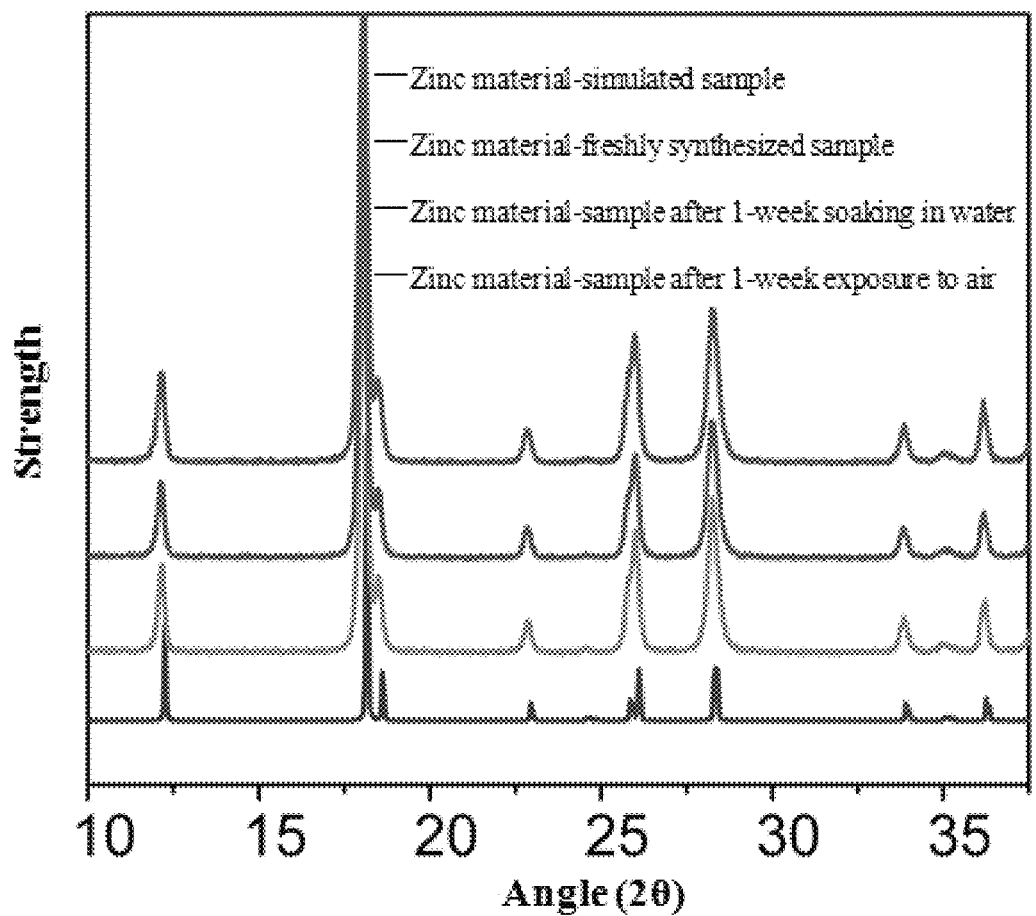
FIG. 1 is an XRD pattern of a metal-organic framework material prepared in Example 1.
Figure 2:
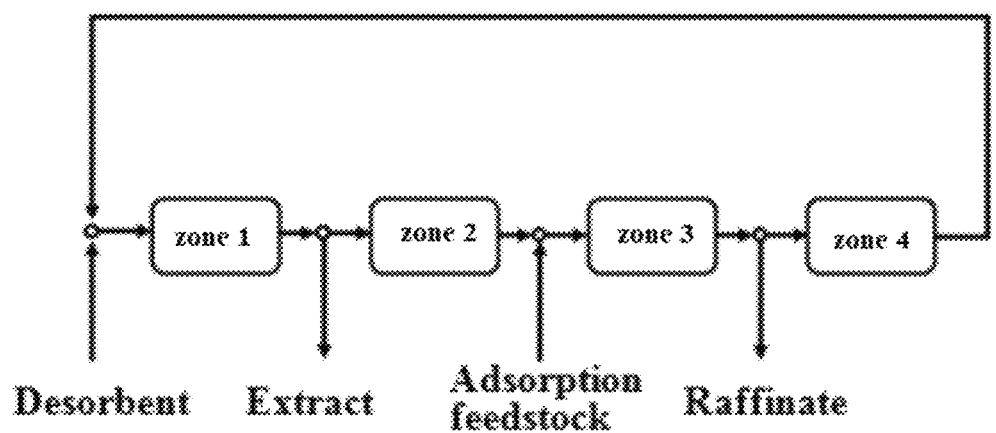
FIG. 2 is a schematic view of a simulated moving bed used in Example 2.
Figure 3:
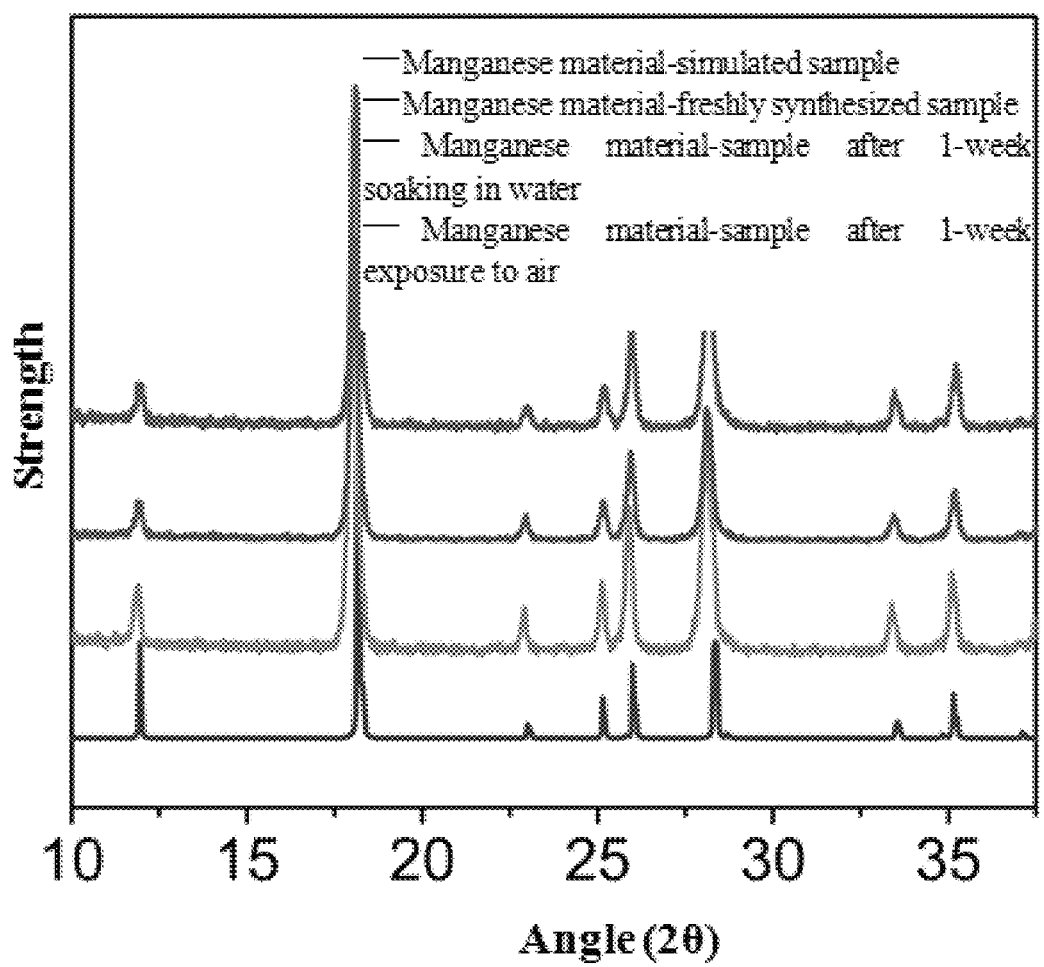
FIG. 3 is an XRD pattern of a metal-organic framework material prepared in Example 2.
Figure 4:
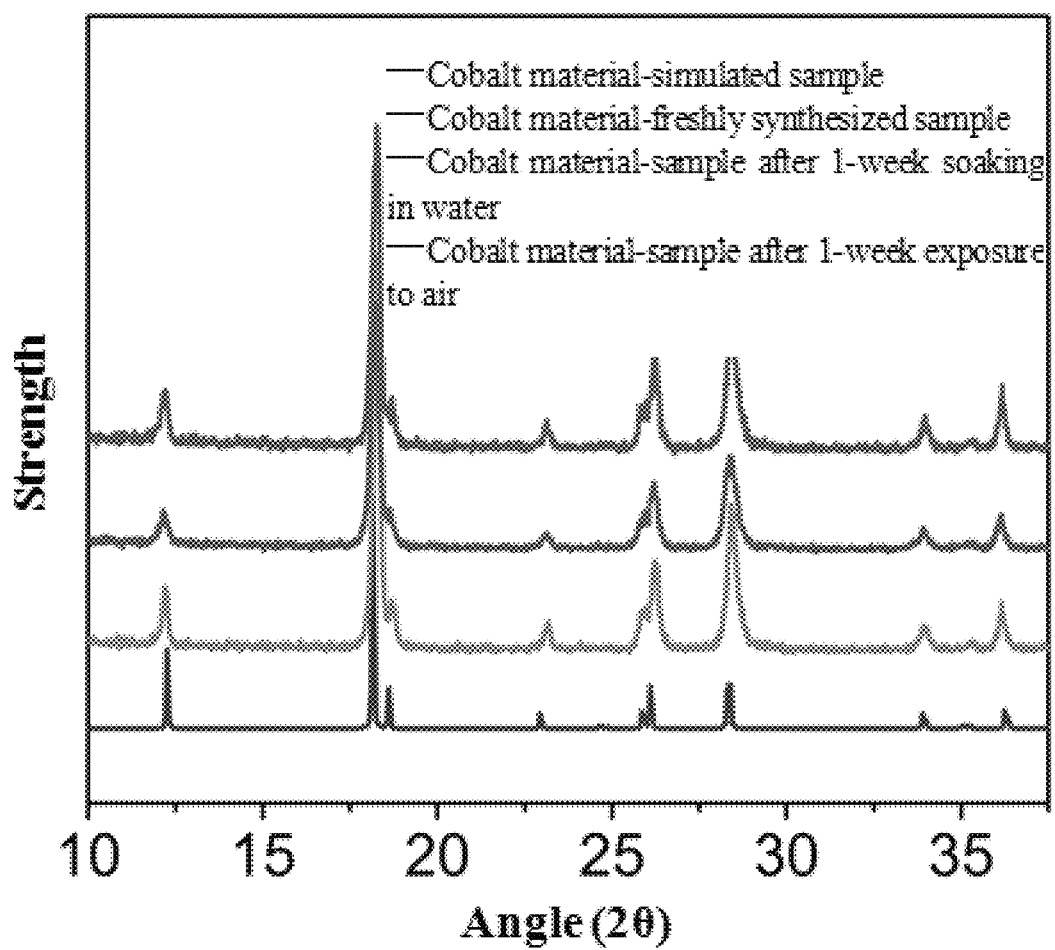
FIG. 4 is an XRD pattern of a metal-organic framework material prepared in Example 3.

The small-scale simulated moving bed unit comprised twelve adsorption columns connected in series. Each column had a length of 150 mm and an inner diameter of 10 mm. A total of 140 mL of the adsorbent was loaded. A circulation pump was connected between two ends of the twelve serially connected columns so that a closed loop was formed, as shown in FIG. 2. In FIG. 2, four incoming and outgoing materials, namely an adsorption feedstock, a desorbent, an extract, and a raffinate, divide the twelve adsorption columns into four sections. That is, the three adsorption columns between the adsorption feedstock (column 8) and the raffinate (column 10) form an adsorption zone; the four adsorption columns between the extract (column 4) and the adsorption feedstock (column 7) form a purification zone; the three adsorption columns between the desorbent (column 1) and the extract (column 3) form a desorption zone; and the two adsorption columns between the raffinate (column 11) and the desorbent (column 12) form a buffer zone. The entire adsorption system was controlled to have a temperature of 150° C. and a pressure of 0.5 MPa.

During operation, p-diethyl benzene as the desorbent as well as the adsorption feedstock were continuously injected into the simulated moving bed unit at flow rates of 130 mL/h and 100 mL/h, respectively; the extract was withdrawn from the unit at a flow rate of 80 mL/h; and the raffinate was withdrawn from the unit at a flow rate of 150 mL/h. The adsorbent feedstock comprised 10 wt % of ethylbenzene, 20 wt % of para-xylene, 50 wt % of meta-xylene, and 20 wt % of ortho-xylene. The circulation pump was set to have a flow rate of 270 mL/h. According to the principle of simulated counter-current chromatography, a position of each of the four materials was shifted forward by one adsorption column every 70 seconds following a liquid flow direction. In the case of a stable operating state, the resulting para-xylene had a purity of 99.75-99.9 wt %, and a recovery rate of para-xylene was 98.0-99.0 wt %.

Example 3

30 mmol of cobalt chloride hexahydrate, 30 mmol of 2,5-dihydroxy-1,4-benzoquinone, and 200 mL of deionized water were mixed and then reacted under stirring at room temperature for 12-24 hours. After the reaction was completed, the resulting solid was centrifugally washed multiple times with deionized water to obtain a purified metal-organic framework material. Measurement and analysis of isotherms of $N_2$ adsorption-desorption on the purified metal-organic framework material at 77 K resulted in a specific surface area of 412.5 m$^2$/g and an average pore size of 5.47-5.54 Å. The purified metal-organic framework material was vacuum degassed at 150° C. for 12 hours to give a solvent-removed adsorbent. Vapor-phase adsorption test was then conducted.

In order to test the adsorptive separation performance of the metal-organic framework material synthesized above, isotherms of adsorption of single-component para-xylene, single-component ortho-xylene, and single-component meta-xylene on the metal-organic framework material as an adsorbent were measured. The adsorption was conducted with an appropriate amount of the adsorbent at temperatures of 30° C., 60° C., 90° C., and 120° C., respectively. At 30° C. and at a single-component saturation vapor pressure of 1000 Pa, para-xylene was adsorbed by an amount of up to 43 mg/g, meta-xylene was adsorbed by an amount of 35 mg/g, and ortho-xylene was adsorbed by an amount of 22 mg/g. At 60° C. and at a single-component saturation vapor pressure of 1000 Pa, para-xylene was adsorbed by an amount of 23 mg/g, meta-xylene was adsorbed by an amount of 23 mg/g, and ortho-xylene was adsorbed by an amount of 11 mg/g. At 90° C. and at a single-component saturation vapor pressure of 1000 Pa, para-xylene was adsorbed by an amount of 14 mg/g, ortho-xylene was adsorbed by an amount of 5 mg/g, and meta-xylene was adsorbed by an amount of 14 mg/g. At 120° C. and at a single-component saturation vapor pressure of 1000 Pa, para-xylene was adsorbed by an amount of 8 mg/g, ortho-xylene was adsorbed by an amount of 1 mg/g, and meta-xylene was adsorbed by an amount of 8 mg/g.

A specific method of separating mixed xylenes with the above synthesized metal-organic framework material is as follows.

The synthesized adsorbent was first molded. An amount of a binder needed in the molding accounted for 3%-10% of a mass of the adsorbent. Breakthrough experiments on a mixed xylenes vapor were conducted using the molded adsorbent. The mixed vapor for adsorptive separation in this example was a mixed vapor of three or two of para-xylene, meta-xylene, and ortho-xylene, with a ratio of saturation vapor pressures of the single-component xylenes being 1:1:1 or 1:1, and a total pressure of the mixed vapor being 0.1 MPa. A packed column had a size of 10 mm I.D.×50 mm, and was packed with about 3.1 g of the molded adsorbent. The test showed that, when the adsorbent was at a temperature of 60° C. and with a saturation vapor pressure ratio of ortho-xylene to meta-xylene to para-xylene being 1:1:1, ortho-xylene and meta-xylene began to pass through the column at 15 minutes, while para-xylene was retained in the packed column for about 100 minutes before beginning to pass through the column. Such a large difference in retention time indicates that the mixed xylenes were effectively separated. After five cycles of adsorption-regeneration, the metal-organic framework material was still stable in its adsorption performance. Conditions for the regeneration were to heat the adsorbent to 150° C. under vacuum or inert atmosphere and keep the adsorbent at the temperature for 72 hours.

Example 4

30 mmol of magnesium acetate hydrate, 30 mmol of 2,5-dihydroxy-1,4-benzoquinone, and 300 mL of deionized water were mixed and then reacted under stirring at room temperature for 24-72 hours. After the reaction was completed, the resulting solid was centrifugally washed multiple times with deionized water to obtain a purified metal-organic framework material. Measurement and analysis of isotherms of $N_2$ adsorption-desorption on the purified metal-organic framework material at 77 K resulted in a specific surface area of 577.2 m$^2$/g and an average pore size of 5.38-5.53 Å. The purified metal-organic framework material was vacuum degassed at 150° C. for 12 hours to give a solvent-removed adsorbent. Vapor-phase adsorption test was then conducted.

In order to test the adsorptive separation performance of the metal-organic framework material synthesized above, isotherms of adsorption of single-component para-xylene, single-component ortho-xylene, and single-component meta-xylene on the metal-organic framework material as an adsorbent were measured. The adsorption was conducted with an appropriate amount of the adsorbent at temperatures of 30° C., 60° C., 90° C., and 120° C., respectively. At 30° C. and at a single-component saturation vapor pressure of 1000 Pa, para-xylene was adsorbed by an amount of up to 79 mg/g, ortho-xylene was adsorbed by an amount of 22 mg/g, and meta-xylene was adsorbed by an amount of 49 mg/g. At 60° C. and at a single-component saturation vapor pressure of 1000 Pa, para-xylene was adsorbed by an amount of 39 mg/g, ortho-xylene was adsorbed by an amount of 12 mg/g, and meta-xylene was adsorbed by an amount of 29 mg/g. At 90° C. and at a single-component saturation vapor pressure of 1000 Pa, para-xylene was adsorbed by an amount of 24 mg/g, ortho-xylene was adsorbed by an amount of 6 mg/g, and meta-xylene was adsorbed by an amount of 19 mg/g. At 120° C. and at a single-component saturation vapor pressure of 1000 Pa, para-xylene was adsorbed by an amount of 13 mg/g, ortho-xylene was adsorbed by an amount of 2 mg/g, and meta-xylene was adsorbed by an amount of 12 mg/g.

A specific method of separating mixed xylenes with the above synthesized metal-organic framework material is as follows.

The synthesized adsorbent was first molded. An amount of a binder needed in the molding accounted for 3%-10% of a mass of the adsorbent. Breakthrough experiments on a mixed xylenes vapor were conducted using the molded adsorbent. The mixed xylenes vapor for adsorptive separation in this example was a mixed vapor of three or two of para-xylene, meta-xylene, and ortho-xylene, with a ratio of saturation vapor pressures of the single-component xylenes being 1:1:1 or 1:1, and a total pressure of the mixed vapor being 0.1 MPa. A packed column had a size of 10 mm I.D.×50 mm, and was packed with about 1.8 g of the molded adsorbent. The test showed that, when the adsorbent was at a temperature of 30° C. and with a saturation vapor pressure ratio of ortho-xylene to meta-xylene to para-xylene being 1:1:1, ortho-xylene and meta-xylene began to pass through the column at 23 minutes, while para-xylene was retained in the packed column for about 96 minutes before beginning to pass through the column and precipitate. Such a large difference in retention time indicates that the mixed xylenes were effectively separated. Conditions for the regeneration were to heat the adsorbent to 150° C. under vacuum or inert atmosphere and keep the adsorbent at the temperature for 72 hours.

Comparative Example 1

15 mmol of nickel acetate hydrate, 15 mmol of 2,5-dihydroxy-1,4-benzoquinone, and 200 mL of deionized water were mixed and then reacted under stirring at room temperature for 24-72 hours. After the reaction was completed, the resulting solid was centrifugally washed multiple times with deionized water to obtain a purified metal-organic framework material. The purified metal-organic framework material was vacuum degassed at 150° C. for 12 hours to give a solvent-removed adsorbent. Vapor-phase adsorption test was then conducted.

Figure 10:
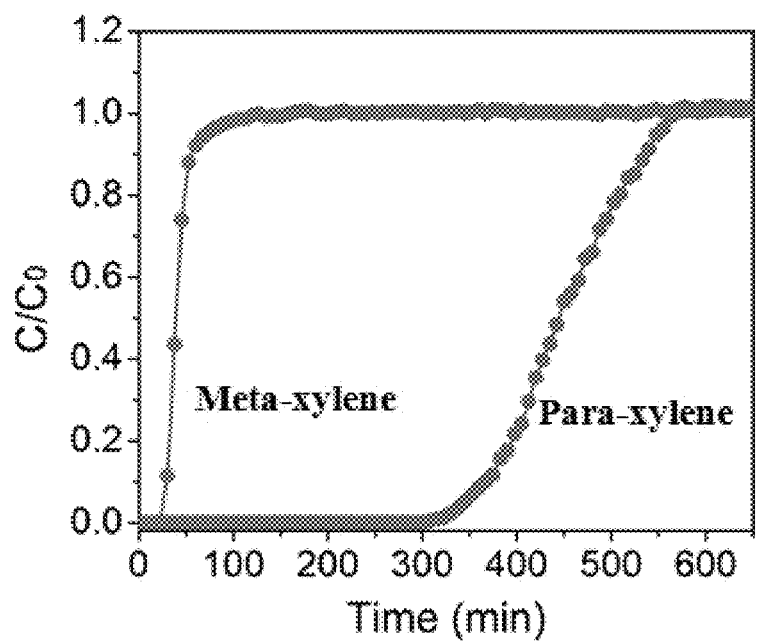
FIG. 10 shows breakthrough curves of meta-xylene/para-xylene through the metal-organic framework material prepared in Example 2 at 90° C.
Figure 11:
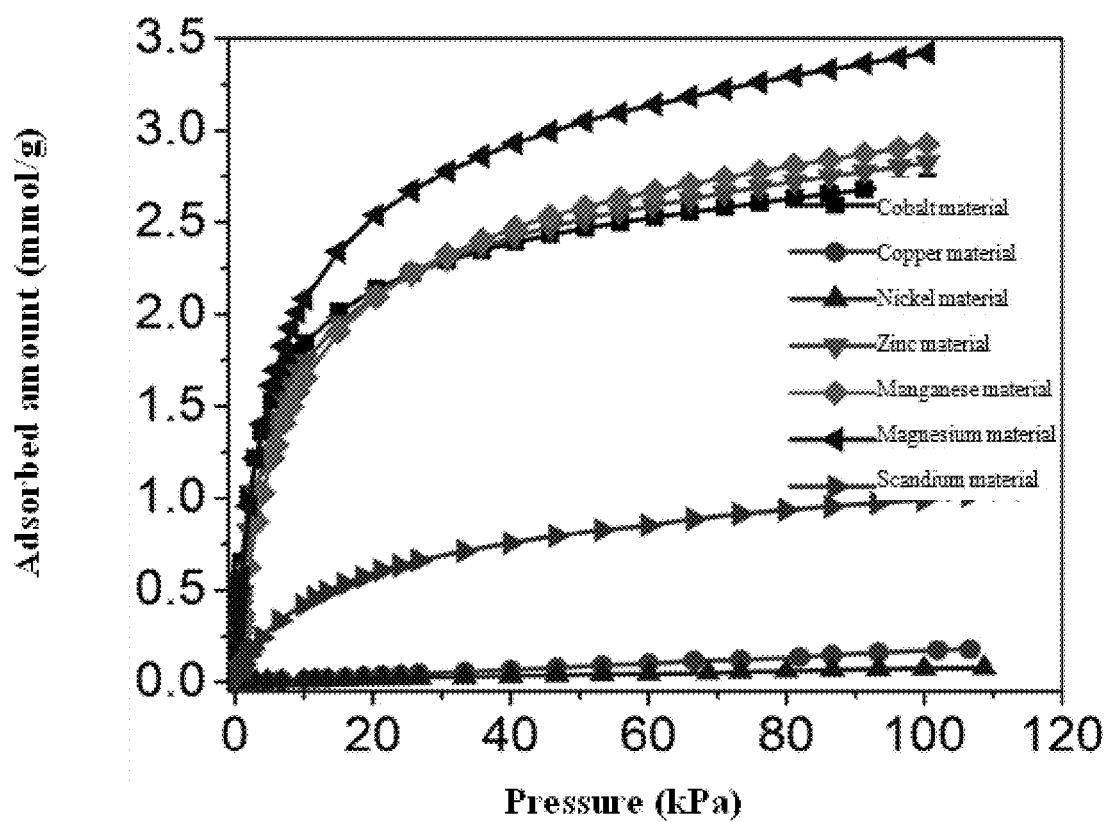
FIG. 11 shows isotherms of adsorption of $CO_2$ on metal-organic framework materials prepared in Examples 1-4 and Comparative Examples 1-2 at 0° C.

In order to test the adsorptive separation performance of the metal-organic framework material synthesized above, isotherms of $CO_2$ adsorption-desorption on the material at 273 K were first measured to examine whether voids were present in the material. As shown in FIG. 10, the metal-organic framework material has no adsorption capacity for the small molecular gas $CO_2$ (3.3 Å in kinetic size), indicating that the material does not have a suitable pore size or that the material has no voids inside for adsorptive separation of xylenes.

Comparative Example 2

1.5 mmol of copper chloride hydrate, 1.5 mmol of 2,5-dihydroxy-1,4-benzoquinone, and 30 mL of deionized water was mixed and then reacted under stirring at room temperature for 24-48 hours. After the reaction was completed, the resulting solid was centrifugally washed multiple times with deionized water to obtain a purified metal-organic framework material. The purified metal-organic framework material was vacuum degassed at 150° C. for 12 hours to give a solvent-removed adsorbent. Vapor-phase adsorption test was then conducted.

In order to test the adsorptive separation performance of the metal-organic framework material synthesized above, isotherms of $CO_2$ adsorption-desorption on the material at 273 K were first measured to examine whether voids were present in the material. As shown in FIG. 10, the metal-organic framework material, like the nickel metal-organic framework material obtained in Comparative Example 1, has an adsorption capacity for $CO_2$ that is close to 0, indicating that the material does not have a suitable pore size or that the material has no voids inside for adsorptive separation of xylenes.

The above described are merely specific embodiments of the present invention, and technical features of the present invention are not limited thereto. Variations or modifications made by any person skilled in relevant arts within the spirit of the present invention shall all fall within the scope of the present invention.

The invention claimed is:

1. A method for separating mixed xylenes, comprising subjecting the mixed xylenes to adsorptive separation by an adsorbent containing a metal-organic framework material to separate one or more xylene isomers from the mixed xylenes,
wherein the metal-organic framework material comprises metal ions and an organic ligand, and wherein the organic ligand comprises 2,5-dihydroxy-1,4-benzoquinone.

2. The method according to claim 1, wherein the metal ions are selected from transition metal ions and alkaline earth metal ions; the mixed xylenes are in gaseous state or liquid state, and comprise two or more compounds selected from ethylbenzene, ortho-xylene, meta-xylene, and para-xylene; and the xylene isomers are one or more compounds selected from ortho-xylene, meta-xylene, and para-xylene.

3. The method according to claim 1, wherein the metal ions comprise one or more selected from zinc ions, manganese ions, cobalt ions, magnesium ions, vanadium ions, zirconium ions, calcium ions, molybdenum ions, chromium ions, iron ions, nickel ions, copper ions, tin ions, niobium ions, titanium ions, and scandium ions.

4. The method according to claim 1, wherein the metal-organic framework material has a pore size of 4 Å or more, and has a specific surface area of 300 $m^2$/g-2000 $m^2$/g.

5. The method according to claim 4, wherein the metal-organic framework material has a pore size of 4 Å-15 Å.

6. The method according to claim 4, wherein the metal-organic framework material has a pore size of 4 Å-10 Å.

7. The method according to claim 1, wherein the adsorptive separation is performed at a temperature of −5° C.-300° C.

8. The method according to claim 1, wherein the adsorptive separation is performed at a temperature of 25° C.-250° C.

9. The method according to claim 1, wherein the adsorptive separation is performed at a temperature of 30° C.-150° C.

10. The method according to claim 1, wherein the adsorptive separation is performed at a pressure of 0.01 MPa-10 MPa.

11. The method according to claim 1, wherein the adsorptive separation is performed at a pressure of 0.1 MPa-6 MPa.

12. The method according to claim 1, wherein the adsorptive separation is performed using a fixed bed, the adsorbent being packed in an adsorption column of the fixed bed.

13. The method according to claim 12, wherein the adsorptive separation comprises the following steps:
(1) passing a mixed xylenes vapor formed by the mixed xylenes and a carrier gas through the adsorption column of the fixed bed, so that a strongly adsorbed xylene isomer in the mixed xylenes is adsorbed on the adsorbent and a weakly adsorbed xylene isomer in the mixed xylenes passes through the adsorption column, thereby obtaining the weakly adsorbed xylene isomer; and (2) desorbing the strongly adsorbed xylene isomer from the adsorbent to obtain the strongly adsorbed xylene isomer.

14. The method according to claim 1, wherein the adsorptive separation is performed using a simulated moving bed, the adsorbent being packed in adsorption zone beds of the simulated moving bed.

15. The method according to claim 14, wherein the adsorptive separation comprises the following step:
(3) passing the mixed xylenes in liquid state through the liquid phase simulated moving bed for adsorptive separation, and withdrawing para-xylene, ortho-xylene, and/or meta-xylene from different beds.

16. The method according to claim 13, wherein the mixed xylenes vapor passes through the adsorption column of the fixed bed at a flow rate of 40-200 mL/min/g adsorbent; and the simulated moving bed has 4-32 adsorbent beds and the ratio of the adsorption zone beds to the desorption zone beds is 1.0-1.5.

17. The method according to claim 1, further comprising regenerating the adsorbent after the adsorptive separation is completed, wherein the regenerating comprises heating the adsorbent to a temperature of 50° C.-300° C. under vacuum or inert atmosphere and keeping the adsorbent at the temperature for 20-120 hours.

* * * * *